US00PP18162P2

(12) United States Plant Patent
Olesen

(10) Patent No.: US PP18,162 P2
(45) Date of Patent: Oct. 30, 2007

(54) FLORIBUNDA ROSE PLANT NAMED 'POULCAS029'

(50) Latin Name: ***Rosa* hybrid**
Varietal Denomination: Poulcas029

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/446,535

(22) Filed: Jun. 2, 2006

(51) Int. Cl.
*A01H 5/00* (2006.01)

(52) U.S. Cl. ..... Plt./150
(58) Field of Classification Search ..... Plt./150, Plt./149
See application file for complete search history.

*Primary Examiner*—Kent Bell

(57) ABSTRACT

A new garden rose plant of the floribunda class which has abundant, pink blended flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas029'.

SUMMARY OF THE INVENTION

The present invention constitutes a new and distinct variety of garden rose plant which originated from a controlled crossing between the female seed parent, an unnamed seedling, and the male pollen parent, a variety by the same inventor named 'Poulcs007', described and illustrated in U.S. Plant Pat. No. 15,161.

The two parents were crossed during the summer of 1995 and the resulting seeds were planted in a controlled environment in Fredensborg, Denmark. The new variety, named 'Poulcas029', originated as a single seedling from the stated cross.

The new variety may be distinguished from its female seed parent primarily by flower color.

The new variety may be distinguished from its male pollen parent 'Poulcs007' by the following combination of characteristics:

1. The pollen parent has a general tonality of flower color of Red Group 49D. The claimed plant has a general tonality of flower color of Red Group 43B with intonations of Red Group 52B.
2. The pollen parent has 75 to 80 flower petals while the claimed plant has 30 to 35 petals, 5 to 8 of which are petaloids.

The objective of the hybridization of this rose variety was to create a new and distinct variety for garden use with unique qualities, such as:

1. Uniform and abundant pink blend flowers;
2. Vigorous, but compact growth when propagated both as a budded rose and on its own roots;
3. Exceptional disease resistance; and
4. Exceptional fragrance.

This combination of qualities is not present in previously available commercial cultivars of this type, known to the inventor, and distinguish 'Poulcas029' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark 'Poulcas029' was selected in the spring of 1996 by the inventor as a single plant from the progeny of the aforementioned hybridization.

Asexual reproduction of 'Poulcas029' by traditional budding and rooted cuttings was first done by Mogens N. Olesen in the nursery in Fredensborg, Denmark in July, 1996. This initial and other subsequent asexual propagations conducted in controlled environments have demonstrated that the characteristics of 'Poulcas029' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas029'.

Specifically illustrated in figure one of the drawing are the typical flower characteristics.

Figure 1:
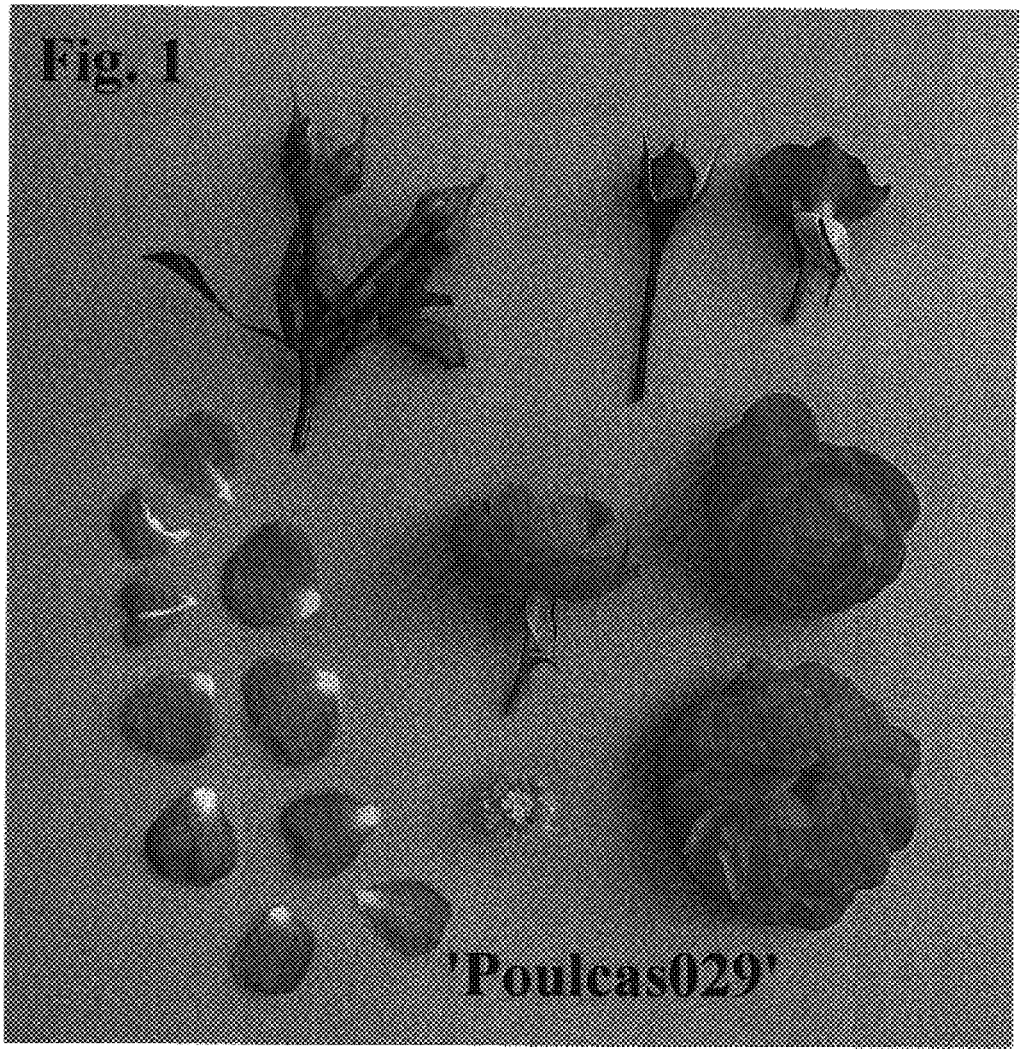
Figure 2:
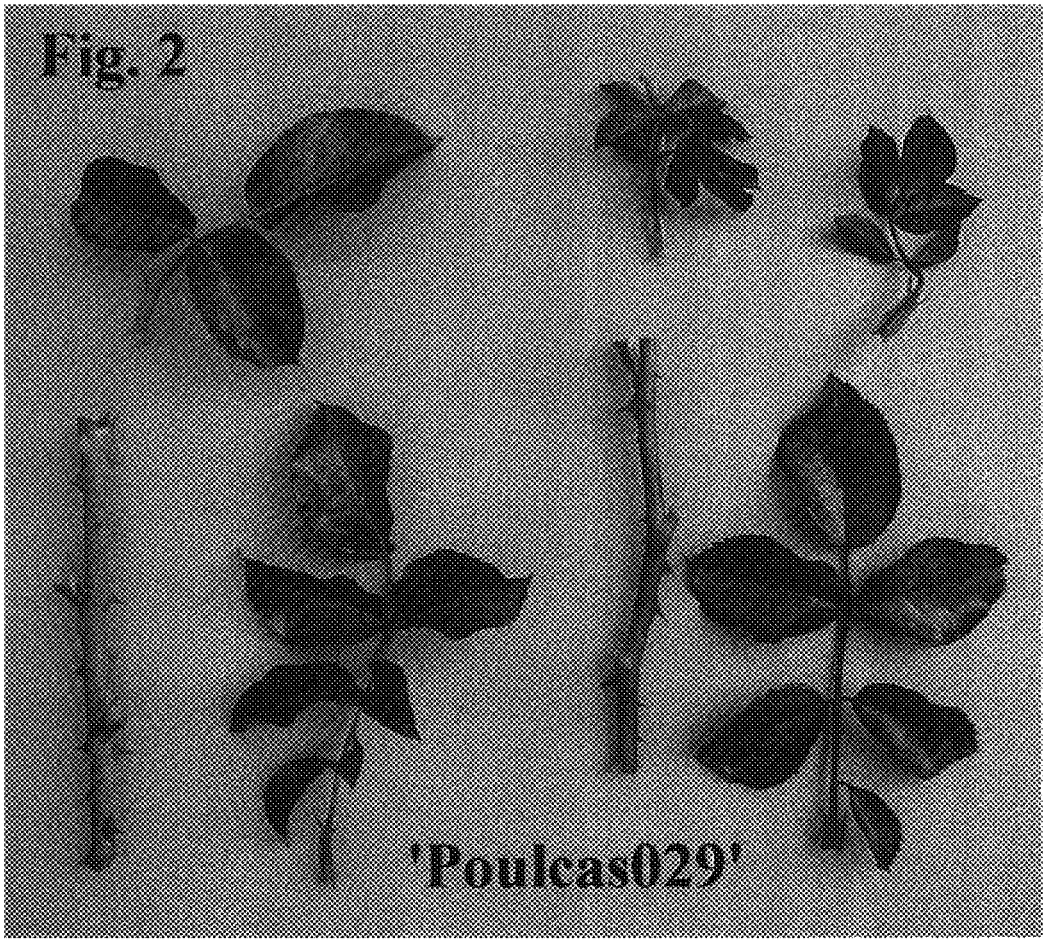

In figure two, the typical characteristics of leaves and stems are shown.

DETAILED DESCRIPTION OF THE VARIETY

The following is a description of 'Poulcas029', as observed in its growth in in a field nursery in Jackson County, Ore. Observed plants are 2 years of age, and were grown on *Rosa multiflora* understock. Color references are made using the Royal Horticultural Society (London, England) Colour Chart, 2001, except where common terms of color are used.

For a comparison, several physical characteristics of the rose variety 'Poulcs016', U.S. Plant Pat. No. 15,748, are compared to 'Poulcas029' in Chart 1.

CHART 1

| | 'Poulcas029' | 'Poulcs016' |
|---|---|---|
| Petal Count | 30 to 35, 5 to 8 of which are petaloids | 25 |
| Fragrance | Strong | Moderate |

CHART 1-continued

| | 'Poulcas029' | 'Poulcs016' |
|---|---|---|
| Color of the upper petal surface, upon opening | Red Group 43C. Occasionally the upper surfaces of petals have streaks the color of Yellow Group 12C. | Red-Purple Group 57C |

FLOWER AND FLOWER BUD

Blooming habit: Continuous.

Flower bud:

*Size.*—Upon opening, normally 30 mm in length from base of receptacle to end of bud. Bud diameter is 16 mm on average

*Bud form.*—Pointed ovoid.

*Bud color.*—As sepals unfold, petals are Orange-Red Group N34A to Red Group 46A with intonations of Greyed-Red Group 179A.

*Sepal inner surface.*—Color: Green Group 138A. Surface: Strong pubescence observed.

*Sepal outer surface.*—Color: Yellow-Green Group 144A. Anthocyanic pigments the color of Greyed-Orange Group 175A and Greyed-Red Group 178A observed. Texture: Rough with many stipitate glands.

*Sepal shape.*—Apex: Cirrhose. Base: Flat at union with receptacle.

*Sepal margin.*—Margins have moderate foliaceous appendages on three of the five sepals.

*Sepal size.*—26 mm long by 9 mm wide on average.

*Receptacle.*—Texture: Smooth. Shape: Funnel shaped. Size: 10 mm in height by 8 mm wide on average. Color: Yellow-Green Group 144A. Anthocyanic pigments the color of Greyed-Orange Group 166A observed.

*Peduncle.*—Length: Normally 8 to 9 cm in length. Diameter: 3 to 4 mm. Texture: Somewhat rough. Color: Yellow-Green Group 146B with anthocyanic intonations of Greyed-Red Group 178A.

Pedicel.—Surface: Rough. Length: 40 mm on average. Diameter: 2.5 mm on average. Color: Yellow-Green Group 144A to 146B. Anthocyanic pigments the color of Greyed-Purple Group 183A observed. Strength: Strong.

Flower bud development: In clusters of 5 flower buds per stem in panicle form.

Flower bloom:

*Fragrance.*—Strong rose perfume.

*Duration.*—The blooms have a duration on the plant of approximately 10 days. Petals fall cleanly away from plant after flowers have fully matured.

*Size.*—Flower diameter is 55 to 75 mm when open. Flower depth is normally 25 mm.

Flower shape.—General shape is calathiform.

*Shape of flower, side view.*—Upon opening the upper portion is somewhat flat. Underneath is a flattened convex. After opening, the upper portion is a flattened convex. The lower portion is concave.

Petalage: Under normal conditions, flowers have 30 to 35 petals total, 5 to 8 of which are petaloids.

Petal color:

*Upon opening, outer and inner petals.*—Upper surface: Red Group 43C. Occasionally the upper surfaces of petals have streaks the color of Yellow Group 12C. Lower surface: Red Group 52B. A slight overlay the color of Red Group 56B is more obvious towards the middle and basal portion of the petal.

*Basal petal spots, upon opening.*—Upper surface: Yellow Group 4B. Lower surface: Yellow Groups 4C.

*After opening, outer and inner petals.*—Upper surface: Red Group 49A to Red Group 52C. Lower surface: Red Group 54B with an overlay of Red Group 56B.

*Basal petal spots, after opening.*—Upper surface: Yellow Group 4D. Lower surface: Yellow Group 4D.

General tonality: On open flower Red Group 43B with intonations of Red Group 52B.

Petals:

*Petal reflex.*—Weak or none.

*Margin.*—Entire and uniform. Young petals have no undulations of margin. As the flower matures, petal margins are increasingly undulated.

*Shape.*—Generally broad elliptical. Apex shape: Round. Base shape: Acute.

*Size.*—28 to 35 mm (l)×22 to 35 mm (w).

*Texture.*—Smooth.

*Thickness.*—Average.

Petaloids:

*Quantity.*—Normally 5 to 8.

*Shape.*—Narrow elliptical and asymmetric. Occasionally there is a deep cleft at the petaloid margin.

*Petaloid color.*—Upper surface: Red Group 43C. Occasionally the upper surfaces of petals have streaks the color of Yellow Group 12C. Lower surface: Red Group 52B. A slight overlay the color of Red Group 56B is more obvious towards the middle and basal portion of the petal.

*Size.*—25 to 35 mm in length by 12 to 20 mm wide.

Reproductive organs:

*Pollen.*—None observed.

*Anthers.*—Size: Normally 2 mm in length. Color: Yellow-Orange Group 14D. Margins of anthers are Greyed-Orange Group 163A. Quantity: 140 on average.

*Filaments.*—Color: Yellow Group 6A. Length: 6 to 7 mm.

*Pistils.*—Length: 6 to 7 mm. Quantity: Normally about 85.

*Stigmas.*—Level in location relative to the length of the filaments and the height of the anthers. Color: Greyed-Yellow Group 160A.

*Styles.*—Color: White Group 155A to Greyed-Green Group 192D.

*Hips.*—None Observed in the field nursery in Jackson County Oreg.

PLANT

Plant growth: Upright and bushy. When grown as a budded field grown plant on *Rosa multiflora* understock, the average height of the plant is 60 to 100 cm and the average width is 60 to 100 cm.

Stems:

*Color.*—Juvenile growth: Greyed-Purple Group 183B and Yellow-Green Group 144B. Mature growth: Yellow-Green Group 146B.

*Diameter.*—Typically 7 mm.

*Internodes.*—On mature canes, 35 to 45 mm between nodes.

*Surface texture.*—Young wood: Smooth. Older wood: Somewhat rough.

Prickles:

*Incidence.*—Normally about 12 prickles per 10 cm of stem.

*Size.*—Average length of prickles on mature stems is 7 mm.

*Shape.*—Upper side is flat, while the lower portion is concave.

*Color.*—Juvenile prickles: Greyed-Red Group 180A. Mature prickles: Greyed-Orange Group 167B.

Plant foliage: Normal number of leaflets in middle of the stem: 7 leaflets.

*Compound leaf.*—145 mm (l) and 95 mm (w).

*Quantity.*—3 leaves per 10 cm of stem on average.

*Color of mature foliage.*—Upper side: Yellow-Green Group 146A. Lower side: Yellow-Green Group 147C.

*Color of juvenile foliage.*—Upper side: Green Group 137A to Green Group 147B. Anthocyanic pigments observed on the margins and mid vein the color of Greyed-Purple Group 187A. Lower side: Yellow-Green Group 144A with anthocyanin generalized throughout the leaflet the color of Greyed-Purple Group 183A.

Plant leaves and leaflets:

*Stipules.*—Size: 23 mm in length. Quantity: 2 per compound leaf. Shape: Linear, slightly broad based with outward extending apecies. Margins: Finely serrated with few stipitate glands. Color: Yellow-Green Group 146C.

*Petiole.*—Length: Normally 35 mm. Diameter: 2.5 mm on average.

*Upper surface.*—Color: Yellow-Green Group 146C with anthocyanic intonations the color of Greyed-Purple Group 183A.

*Lower surface.*—Color: Yellow-Green Group 144B. Observations: Small prickles observed.

*Rachis.*—Length: Typically 60 mm. Upper surface: Color: Yellow-Green Group 146C with anthocyanic intonations the color of Greyed-Purple Group 183A.

*Lower surface.*—Color: Yellow-Green Group 144B. Observations: Small prickles observed.

*Leaflet.*—Edge: Serrated. Size: Average size of the terminal leaflet on normal leaves is 50 mm in length by 35 mm wide. Shape: Ovate. Base: Rounded. Apex: Cuspidate. Texture: Smooth. Thickness: Thick. Arrangement: Odd pinnate. Venation: Reticulate. Glossiness: Moderately glossy.

Disease resistance: Above average resistance to powdery and downy mildew, rust, black spot, and *Botrytis* under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the floribunda rose class named 'Poulcas029', substantially as illustrated and described herein, due to its abundant pink blended flowers, disease resistance, and extended period of bloom.

* * * * *

'Poulcas029'

'Poulcas029'